Figure 1:
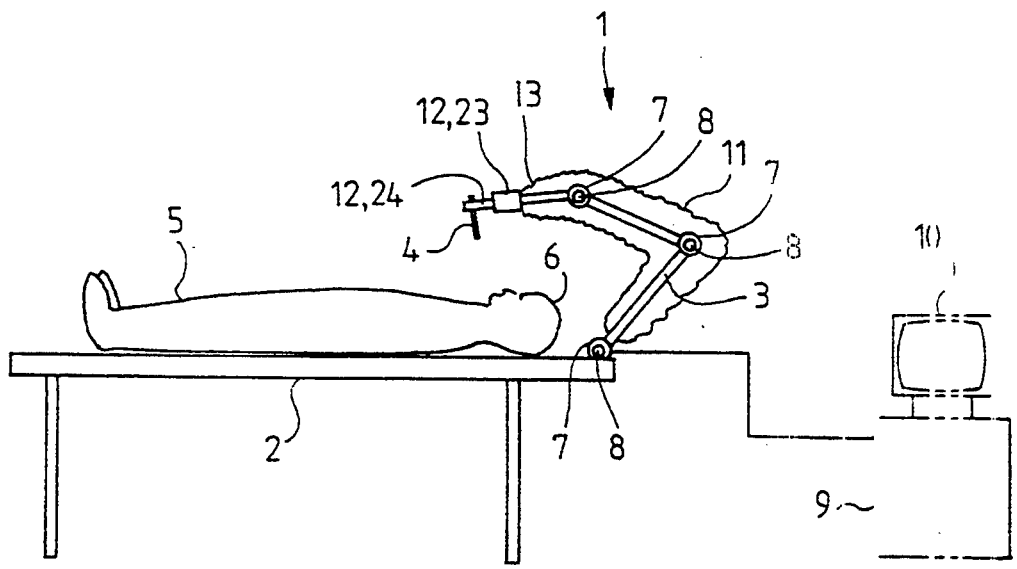

United States Patent

Koivukangas

Patent Number: 5,413,573
Date of Patent: May 9, 1995

[54] DEVICE FOR SURGICAL PROCEDURES

[75] Inventor: John Koivukangas, Oulu, Finland

[73] Assignee: Onesys Oy, Oulu, Finland

[21] Appl. No.: 142,405

[22] PCT Filed: May 22, 1992

[86] PCT No.: PCT/FI92/00162
 § 371 Date: Nov. 24, 1993
 § 102(e) Date: Nov. 24, 1993

[87] PCT Pub. No.: WO92/20295
 PCT Pub. Date: Nov. 26, 1992

[30] Foreign Application Priority Data

May 24, 1991 [FI] Finland .................. 912520

[51] Int. Cl.$^6$ .................. A61B 17/02
[52] U.S. Cl. .................. 606/1; 128/20
[58] Field of Search .................. 606/1; 128/4, 20

[56] References Cited

U.S. PATENT DOCUMENTS

| | | | |
|---|---|---|---|
| 2,733,666 | 11/1955 | Greenberg | 606/205 X |
| 3,643,655 | 2/1972 | Peronti | 128/20 |
| 4,143,652 | 3/1979 | Meier et al. | 128/20 |
| 4,522,196 | 6/1985 | Cunningham et al. | 128/4 |
| 4,817,592 | 4/1989 | Auchinleck et al. | 128/20 X |
| 4,825,850 | 5/1989 | Opie | 128/4 |
| 4,827,926 | 5/1989 | Carol | 128/4 X |
| 5,239,981 | 8/1993 | Anapliotis | 128/4 |
| 5,280,782 | 1/1994 | Wilk | 128/30 |

FOREIGN PATENT DOCUMENTS

| | | | |
|---|---|---|---|
| 0326768 | of 0000 | European Pat. Off. | |
| 293760 | 12/1988 | European Pat. Off. | 606/1 |
| 210136 | of 0000 | Sweden. | |

Primary Examiner—Peter A. Aschenbrenner
Attorney, Agent, or Firm—Brumbaugh, Graves, Donohue & Raymond

[57] ABSTRACT

The invention relates to a surgical procedures device in connection with a medical procedure, the device comprising an orientation arm (3) adapted to be used for performing and/or guiding the movements required by the procedure, and said orientation arm (3) being protected or protectable by means of a sterile or sterilizable protection means (11), and to which orientation arm (3) or equivalent means a surgical instrument (4), such as a needle, an ultrasonic probe or equivalent means is connected or connectable, and the orientation arm (3) being connected or connectable to the surgical instrument (4) by means of an intermediate piece (12) or equivalent, made of a sterilizable material. The intermediate piece (12) and orientation arm (3) comprise identification means (15, 16) for generating an identification signal specific to the surgical instrument and for permitting the identification of the surgical instrument (4).

6 Claims, 2 Drawing Sheets

DEVICE FOR SURGICAL PROCEDURES

The invention relates to a device for surgical procedures, used for instance in connection with brain surgery or other medical procedure, the device comprising an orientation arm or equivalent means adapted to be used for performing and/or guiding the movements required by the procedure, and said orientation arm being protected or protectable by means of a sterile or sterilizable protection means, such as a protective bag, protective sleeve or equivalent means, and to which orientation arm or equivalent means a surgical instrument, such as an indicator, ultrasonic probe or equivalent means is connected or connectable.

The present device for surgical procedures can be utilized for instance in neurosurgical operations, i.e. surgery on the human brain. Very stringent and exacting requirements have been set on equipment used in medicine in regard to their operation, safety in use and safety for patients as well as hygiene. Equipment used in surgery must also be reliable in use and functional to the surgeon performing the operation.

Presently e.g. in brain surgery computer aided methods and equipment making use of digital imaging technology and interactive computers are used. The methods employ for instance computer tomography and magnetic resonance imaging. After the imaging procedure, the data obtained is transposed to a computer wherein said data is edited. The present device for surgical procedures is suitable for use for instance in connection with sophisticated surgical methods and devices of the above-stated kind.

The devices according to the prior art include a surgical orienter comprising an arm, the surgical instrument at the end of said arm being movable over a patient's head by moving this arm. In sophisticated equipment, the orientation arm comprises at its articulated points sensors on the basis of which the computer equipment connected to the device knows the location of the orientation arm and thereby the location of the instrument, and thus, for instance in the graphing of a patient's head, the site of the surgical instrument can be located on the screen by means of the equipment. The orientation arm is normally made of an unsterile material, or the sterilization of the orientation arm is not possible or at least cannot readily be carried out, and therefore the orientation arm is covered by a sterile protection means, such as a sterile protective sleeve.

In certain equipment according to the prior art, the surgical instruments to be used in an operation are connected to the orientation arm directly through the protective sleeve, the surgical instrument—such as a needle, an ultrasonic sensor or other equivalent instrument—being fixed to the orientation arm, so that the sterile sleeve protecting the orientation arm remains between the orientation arm and the surgical instrument. However, for example in the preparation of brain surgery operations and in the actual performance of said operations, the need arises for exchanging the surgical instrument disposed at the end of the orientation arm for another surgical instrument. Yet the durability of the sterile protective sleeve is limited, and therefore, consequent on the several detachings and fixings, a hole may be produced in the protective sleeve as a result of wear, on account of which the unsterile orientation arm is no longer insulated from the sterile surgical instrument. The fact that the protective sleeve is squeezed between the orientation arm and the surgical instrument is a cause of wear. From the point of view of the patient operated upon, the unsterility will constitute a considerable hazard to the success of the surgery and thereby to the health of the patient.

Patents EP 0 293 760 and EP 0 326 768 disclose devices for use in surgery, incorporating an intermediate piece between an orientation arm and a surgical instrument, wherewith the circumstance can partly be improved. In said arrangements, however, the intermediate piece is of the kind of a passive intermediate piece.

The drawbacks and defects of the prior art are many. Moreover, nowadays the interface between the unsterile and sterile field is of a passive kind, and no other operations are carried out at the interface than the connection of the different parts to one another. In the present prior art equipment, the realization of the linkage between the unsterile and sterile field presents a problem. It would be significant for the operational safety of the equipment that the observation and surveillance of the exchange of the surgical instrument were automatic, which however is not the case with the existing equipment. It would also be important from the point of view of the computing properties of the computer equipment processing the graphing data that the exchange of the surgical instrument were readily observed. It would be desirable that the observation and recording of the exchange of the surgical instrument required no steps from the part of the persons performing the surgery, especially when the actual surgical operation is in progress and the attention of the surgeon and the other personnel carrying out the surgery is naturally directed to performing the actual surgical operation.

It is the object of this invention to provide a novel device for surgical procedures, obviating the problems and drawbacks involved in the prior art devices.

This object is achieved with the device of the invention for surgical procedures, which is characterized in that the intermediate piece and orientation arm comprise identification means for generating an identification signal specific to the surgical instrument and for permitting the identification of the surgical instrument.

The device for surgical procedures according to the invention is based on the idea that means wherewith the surgical instruments can be readily identified are disposed in the interface between the sterile and unsterile fields.

Several advantages are achieved with the device of the invention for surgical procedures. The apparatus according to the basic idea of the invention permits the functioning of the field between the unsterile and sterile fields also in other use than merely as a passive junction zone between the different parts. The connection of the sterile surgical instruments to the sterile-covered unsterile parts, such as an orientation arm, is easy to carry out and safe from the point of view of sterility. In the device for surgical procedures according to the present invention, the protective sleeve or equivalent means protecting the unsterile parts is not subjected to as high stresses as in the equipment of the prior art, and thus the protective sleeve will not wear to an equal extent in use.

Figure 2:
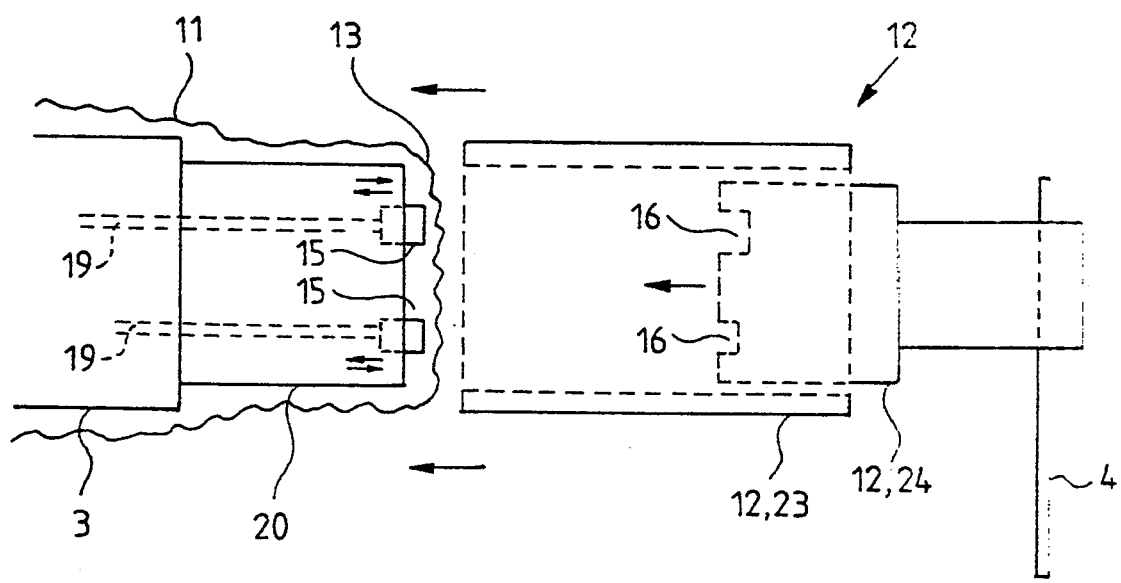
Figure 3:
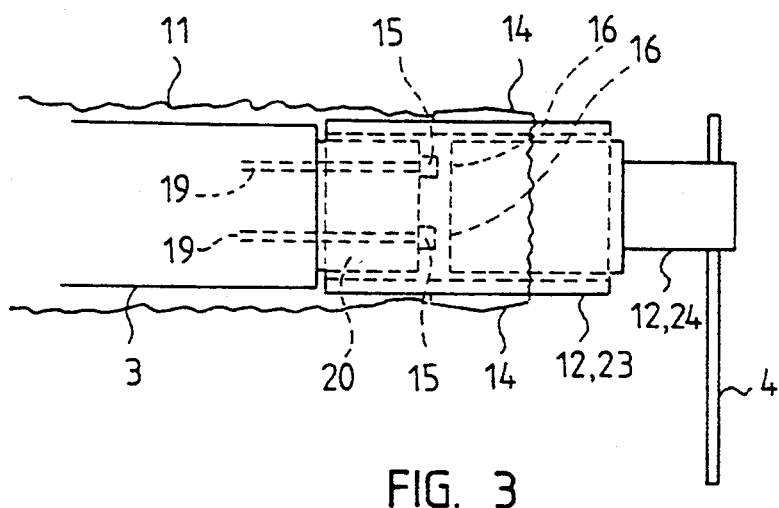
Figure 4:
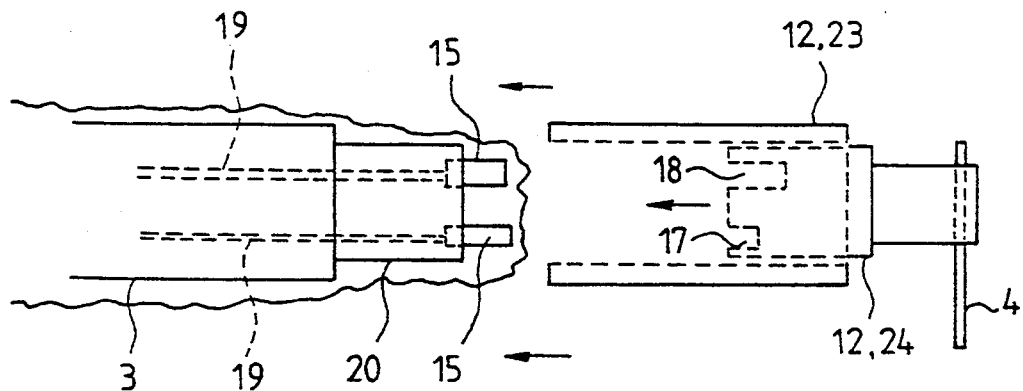
Figure 5A:
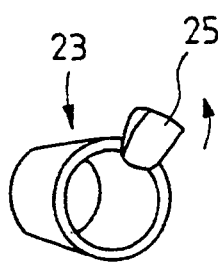
Figure 5B:
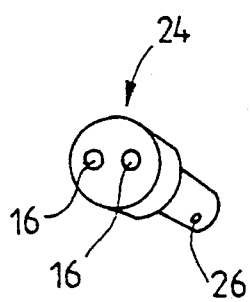
Figure 5C:
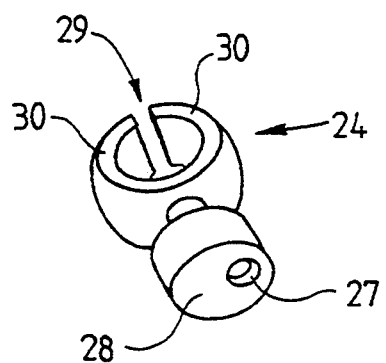

The invention will be explained in more detail in the following with reference to the accompanying drawings, wherein FIG. 1 shows a device for surgical procedures and its operating environment, FIG. 2 is a schematic side view of the positioning of an intermediate piece between an orientation arm and a surgical instrument, FIG. 3 is a schematic side view of the positioning of the intermediate piece, FIG. 4 is a schematic side view of the positioning of the intermediate piece, FIG. 5a shows a frame member incorporated in the intermediate piece, FIG. 5b shows one contact member for the intermediate piece, FIG. 5c shows another contact member for the intermediate piece.

In accordance with FIG. 1, the device 1 for surgical procedures is arranged in connection with an operating table 2 in an operating room. The device 1 for surgical procedures comprises for instance an orientation arm 3 connected to a surgical instrument 4. The orientation arm 3 is only one of the possible means by which the surgical instrument 4 is moved, and thus the invention is naturally not limited to devices for surgical procedures using an orientation arm 3. What is essential is that the device 1 for surgical procedures comprises means for moving the surgical instrument 4.

FIG. 1 shows as the surgical instrument 4 a probe or a guide for biopsy forceps, through which a sample can be taken from the head 6 of a patient 5 lying on the operating table 2. Other possible surgical instruments include an ultrasonic sensor, a surgical adapter, an endoscope or a surgical microscope and laser equipment in connection therewith.

The orientation arm 3 is employed for moving the surgical instrument 4. The orientation arm 3 is articulated and comprises at its articulation points 7 position sensors 8 measuring the movement and position of the orientation arm 3. The information received from the position sensors on the position of the orientation arm 3, i.e. in practice on the position of the surgical instrument 4 with the orientation arm 3, is fed into computer equipment 9. Imaging data on the structure of the patient's head have previously been stored in the computer equipment 9 by means of MRI (Magnetic Resonance Image) scan, for instance. The position information received from the position sensors 8 of the orientation arm 3 constitutes one parameter in the operation of the computer equipment 9, for instance so as to enable the presentation position of the surgical instrument 3 in relation to the structure of the patient's head in the imaging data for instance on a screen 10 connected to the computer equipment, the surgeon performing the surgery thus being able to see from the screen 10 in real time the position of the surgical instrument 4.

The orientation arm 3 is unsterile, wherefore it is covered by a sterile protection means 11. The protection means 11 may be a plastic protective sleeve or protective bag, for instance. In the device i for surgical procedures, the orientation arm 3 is connected to the surgical instrument 4 by means of an intermediate piece 12 or equivalent, made of a sterilizable material, which is thus adapted to connect the unsterile but sterile-covered orientation arm 3 and the sterile surgical instrument 4. The manufacturing material of the intermediate piece 12 may be a metal or plastic, such as teflon or polyacetal.

The orientation arm 3 may be protected by a sterile protective sleeve 11 in such a way that the end of the orientation arm is located at the closed bottom 13 of the protective sleeve, and thus the entire intermediate piece 12 is located outside the protective sleeve 11 in accordance with FIG. 2. In that event, the end of the orientation arm 3 and the end of the intermediate piece 12 on the orientation arm side are so shaped that the members can clamp one another, and further so that the protective bag 11 remains between the members in accordance with FIG. 2. FIG. 2 shows, for enhanced graphicity, the orientation arm 3 and the intermediate piece 12 as detached from one another.

Alternatively, in accordance with FIG. 3 the protective sleeve 11 may have an open end, but in that event the open edges of the protective sleeve 11 are fixed e.g. with tape 14 or adhesive, to close the bag, one possible embodiment in accordance with FIG. 3 then being to tape the edges of the protective sleeve 11, i.e. the protective bag, to the intermediate piece 12, and thus at least a portion of the intermediate piece 12 will remain within the protective sleeve 11.

FIG. 2 shows in closer detail the positioning of the intermediate piece between the orientation arm 3 and the instrument 4. In accordance with the invention, the intermediate piece 12 and the orientation arm 3 comprise identification means 15, 16 for identifying the surgical instrument 4 to be attached to the intermediate piece 12. Thus the intermediate piece 12 is not merely a mechanical connecting piece, but the intermediate piece 12 and/or the orientation arm 3 further comprises mechanical, electrical, optical or other identification means wherewith each surgical instrument 4 or other device connected to the intermediate piece 12 can be identified. The identification data thus obtained can be transposed to the computer equipment 9 to which the device for surgical procedures is connected, said computer equipment thereby receiving automatically information on which instrument 4 is connected to the intermediate piece 12 in each case. By means of the identification means, definitely correct information is always obtained for the computer equipment 9 as to which surgical instrument 4 or other device is connected to the orientation arm 3 by means of the intermediate piece 12.

In one preferred embodiment, the identification means comprise one or more switch means 15 arranged at the end of the orientation arm 3 or in the vicinity thereof, and one or more contact means 16 arranged in the intermediate piece, the contact information provided by which is dependent on the surgical instrument 4 connected to the intermediate piece 12.

In a preferred embodiment of the invention, the switch means 15 incorporated in the orientation arm 3 are press switches intended for connecting an electric signal, and the contact means 16 incorporated in the intermediate piece 12 are shapes produced in the intermediate piece 12, such as apertures and/or protuberances and/or flat zones adapted to push or not push the press switches. If the contact means 16 in the intermediate piece 12 is an aperture, the press switch 15 constituting the switch means will be seated in the aperture 16, and thus the press switch is not depressed and will not give a signal. If the contact means 16 in the intermediate piece 12 is a flat zone or a protuberance, pressure is applied to the press switch 15 constituting the switch means, and thus the press switch will give a signal. Four different combinations can be achieved with two pairs of switch means and contact means. If the combinations are looked at from the point of view of the switch means 15, the combinations are: neither of the switches contacts, the first switch contacts, the second switch contacts, and as a fourth combination a situation where both switches contact. Correspondingly, in view of the sequence for the combinations of switches, if the situation is looked at from the point of view of the contact means 16 of the intermediate piece 12 and the apertures and the flat zone of the intermediate piece 12 are utilized, the four combinations are: both are apertures, the first is a flat zone and the second an aperture, the first is an aperture and the second a flat zone, and as a fourth combination a situation where both contact means are flat zones. It can be specified for the computer equipment 9 which combination signifies which surgical instrument. In FIG. 3, two flat zones are to be seen as contact means 16.

However, the use of both apertures and flat zones/protuberances simultaneously is not necessary, as the different combinations can be realized in accordance with FIG. 4 for instance in such a way that a normal aperture 17 and a still deeper aperture 18 are used as contact means in the intermediate piece 12, the normal aperture 17 being so low that the press switch 15 is depressed and gives a signal, and the deep aperture 18 being so deep that the press switch 15 is not depressed and does not give a signal. The possible signal is connected to the computer equipment 9 by means of conductors 19. The conductors 19 can be conveyed together with the orientation arm 3 or within it, and thus the conductors 19 will not disturb the performing of the operations. The computer equipment 9 comprises the necessary means, for instance a logic circuit, for measuring and interpreting the signals received from the switch means 15, and thus the computer equipment 9, when handling the patient imaging data, utilizes data received from the identification means 15, 16 as to which surgical instrument 4 in each case is connected to the orientation arm 3 through the intermediate piece 12.

In a preferred embodiment of the invention, the orientation arm 3 or its tip comprises a projection 20 which extends from the orientation arm 3 and in which the switch means are arranged; thus the projection 20 in practice constitutes the tip of the orientation arm 3. On account of the projection 20 of the orientation arm 3, the switch means 15 are readily accessible, and, furthermore, the intermediate piece can be better and more easily seated in the orientation arm 3.

The intermediate piece 3 is advantageously constituted by at least two interconnectable parts, the first part being a frame member 23 or equivalent and being disposed about the end of the orientation arm 3 protected by a protection means 11, i.e. about the projection 20. In accordance with FIGS. 4 and 5, one embodiment of the device of the invention is such wherein the projection 20 of the orientation arm 3 has an external shape of a cylinder, the frame member 23 of the intermediate piece 12 being a hollow member and cylindrical at least on the inside, that is, follows the shape of the exterior of the projection 20 of the orientation arm 3, and thus the frame member 23 of the intermediate piece 12 can be disposed on the projection 20. The frame member of the intermediate piece 12 constitutes a frame for the mounting of the other part of the intermediate piece 12, i.e., a contact member 24. The frame member 23 of the intermediate piece 12 is constructed to have such a length that the frame member can accommodate the end or projection 20 of the orientation arm 3 entering from one direction as well as the contact member 24 of the intermediate piece 12 entering the frame member 23 from the opposite direction. The frame member 23 of the intermediate piece 12 may be similar for all surgical instruments 4, but the other part of the intermediate piece 12, i.e. the contact member 24, is an interchangeable contact member 24 incorporating contact means 16, that is, apertures and/or flat zones and/or protuberances, and specific to each surgical instrument 4, being adaptable to the frame member 23 so that the contact means 16 incorporated in the contact member 24 communicate with the switch means 15 incorporated in the orientation arm 3 through the protection means 11 protecting the orientation arm 3. During the surgery, the frame member 23 will remain stationary, but different contact members—such as those shown in FIGS. 5b and 5c—can be exchanged within the frame member, if the need arises to exchange the surgical instrument during the surgery.

FIG. 5a shows a frame member 23. The cylindrical and hollow frame member 23 further comprises locking means 25 or equivalent, by means of which the frame member 23 and the contact member 24 can be interlocked. The locking means 25 is a push-button; the locking will be released when the button is pressed. The push-button is advantageously made of the same e.g. plastic mould as the actual contact member, and thus when the push-button is pressed it behaves resiliently and permits the detachment of the frame member 23 and the contact member 24. The contact member 24 has a stepped shape, and thus the point of the push-button 25 extending further than the inner periphery of the frame member will lock the contact member 24 to the frame member 23 on account of the stepping.

FIGS. 5b and 5c show two different contact members 24. As many contact members can be manufactured as there are various surgical instruments.

The contact members 24 incorporate at their one end contact means 16, i.e. apertures, flat zones or protuberances, for instance, and at its opposite end the contact member 24 incorporates attachment means 26 to which the surgical instrument can be attached.

FIG. 5b shows a coupling member for a biopsy guide, incorporating two apertures 16 provided in the contact member as contact means, and a hole for the biopsy guide as an attachment means 26 at the other end.

FIG. 5c shows a contact member for an ultrasonic sensor or other surgical instrument or device having a rounded housing, wherein the contact means is constituted by one aperture 27 and a flat zone 28, and the attachment means shown is a substantially circular aperture 29 with edges 30, in the aperture defined by which the surgical instrument can be positioned.

In a preferred embodiment of the invention, the distance of the end of the contact member on the orientation arm side from the main axis of the point of attachment of the surgical instrument in each different contact member is the same as in the other contact members. Thereby one achieves that the computer is not required to compute both the imaging data and the location of the instrument on the screen if the instrument is exchanged.

Even though the invention has been explained in the foregoing with reference to examples according to the accompanying drawings, it is evident that the invention is not limited thereto, but it can be modified in many ways within the scope of the inventive concept set forth in the appended claims.

I claim:

1. A device for performing surgical procedures comprising:

orientation means for guiding movements to perform said surgical procedures;

a surgical instrument for performing a selected one of said surgical procedures;

an intermediate piece having two ends, said intermediate piece being engageable with the orientation means at one of said ends and connected to said surgical instrument at the other end;

means connected to the orientation means for generating at least one signal; and identification means carried by the intermediate piece for causing the generating means to generate said at least one signal when said orientation means is engaged with said intermediate piece, said at least one signal identifying said surgical instrument;

whereby said at least one signal is read to ensure propriety of said surgical instrument to be used for the selected surgical procedure.

2. A device according to claim 1, wherein the identification means further comprises switch means disposed on a first surface on the orientation means, and contact means (16) disposed on a second surface on the intermediate piece for enabling said switch means when said orientation means is engaged with said intermediate piece.

3. A device according to claim 2, wherein at least the switch means is protected by sterilizable protection means.

4. A device according to claim 2, wherein said at least one signal comprises electrical signals, said generating means including a plurality of electrical circuits, the switch means including switches for closing said electrical circuits when said switches are enabled, being shaped in such a way that a selected combination of said switches are enabled when said switch means is engaged with said contact means.

5. A device according to claim 2 or 4, wherein the orientation means further comprises a projection on an end thereof, said projection having said first surface.

6. A device according to claim 2, wherein the intermediate piece further comprises a frame member and an interchangeable contact member, said frame member engageable with the orientation means, said interchangeable contact member having said second surface and being engageable with said frame member, said contact means being associated with said surgical instrument, whereby when the frame member is engaged with the orientation means, the contact means selectively enables the switch means.

* * * * *